United States Patent
Weinschenk, III et al.

(10) Patent No.: US 8,012,204 B2
(45) Date of Patent: Sep. 6, 2011

(54) ACCOMMODATIVE INTRAOCULAR LENS SYSTEM

(75) Inventors: Joseph Weinschenk, III, Fort Worth, TX (US); Xiaoxiao Zhang, Fort Worth, TX (US)

(73) Assignee: Novartis AG, Basel (CH)

( * ) Notice: Subject to any disclaimer, the term of this patent is extended or adjusted under 35 U.S.C. 154(b) by 166 days.

(21) Appl. No.: 12/269,960

(22) Filed: Nov. 13, 2008

(65) Prior Publication Data

US 2009/0125106 A1   May 14, 2009

Related U.S. Application Data

(60) Provisional application No. 60/987,822, filed on Nov. 14, 2007.

(51) Int. Cl.
*A61F 2/16* (2006.01)

(52) U.S. Cl. .................. 623/6.34; 623/6.4

(58) Field of Classification Search .......... 623/6.32, 623/6.34–6.41
See application file for complete search history.

(56) References Cited

U.S. PATENT DOCUMENTS

| | | | |
|---|---|---|---|
| 5,275,623 A | 1/1994 | Sarfarazi | |
| 5,476,514 A | 12/1995 | Cumming | |
| 5,496,366 A | 3/1996 | Cumming | |
| 5,607,472 A * | 3/1997 | Thompson | 623/6.13 |
| 5,674,282 A | 10/1997 | Cumming | |
| 6,197,059 B1 | 3/2001 | Cumming | |
| 6,241,777 B1 | 6/2001 | Kellan | |
| 6,261,321 B1 | 7/2001 | Kellan | |
| 6,302,911 B1 | 10/2001 | Hanna | |
| 6,464,725 B2 * | 10/2002 | Skotton | 623/6.34 |
| 6,645,246 B1 | 11/2003 | Weinschenk | |
| 2002/0107568 A1 * | 8/2002 | Zadno-Azizi et al. | 623/6.37 |
| 2002/0177896 A1 * | 11/2002 | Israel | 623/6.37 |
| 2003/0135272 A1 * | 7/2003 | Brady et al. | 623/6.37 |
| 2003/0187504 A1 * | 10/2003 | Weinschenk et al. | 623/6.22 |
| 2004/0111151 A1 * | 6/2004 | Paul et al. | 623/6.37 |
| 2004/0148023 A1 * | 7/2004 | Shu | 623/6.34 |
| 2006/0155373 A1 * | 7/2006 | Israel | 623/6.4 |
| 2006/0161252 A1 * | 7/2006 | Brady et al. | 623/6.37 |
| 2007/0050024 A1 * | 3/2007 | Zhang | 623/6.34 |

FOREIGN PATENT DOCUMENTS

| WO | WO 00/66037 | 11/2000 |
|---|---|---|
| WO | WO 01/34067 | 5/2001 |

* cited by examiner

*Primary Examiner* — David H Willse
*Assistant Examiner* — Tiffany Shipmon
(74) *Attorney, Agent, or Firm* — Jonathan E. Prejean

(57) ABSTRACT

A two optic accommodative lens system wherein at least one of the optics is deformable. When compressed by the capsular bag, the two optics press against each other, deforming at least one of the optics. As a result, the interface where the two optics meet changes shape, thereby altering the refractive power of the lens system.

5 Claims, 4 Drawing Sheets

ACCOMMODATIVE INTRAOCULAR LENS SYSTEM

This application claims the priority of U.S. Provisional Application No. 60/987,822 filed Nov. 14, 2007.

BACKGROUND OF THE INVENTION

This invention relates generally to the field of intraocular lenses (IOL) and, more particularly, to accommodative IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can be focused alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Prior to the present invention, when a cataract or other disease required the removal of the natural lens and replacement with an artificial IOL, the IOL was a monofocal lens, requiring that the patient use a pair of spectacles or contact lenses for near vision. Advanced Medical Optics has been selling a bifocal IOL, the ARRAY lens, for several years, but due to quality of issues, this lens has not been widely accepted.

Several designs for accommodative IOLs are being studied. For example, several designs manufactured by C&C Vision are currently undergoing clinical trials. See U.S. Pat. Nos. 6,197,059, 5,674,282, 5,496,366 and 5,476,514 (Cumming), the entire contents of which are incorporated herein by reference. The lens described in these patents is a single optic lens having flexible haptics that allows the optic to move forward and backward in reaction to movement of the ciliary muscle. Similar designs are described in U.S. Pat. No. 6,302,911 B1 (Hanna), U.S. Pat. Nos. 6,261,321 B1 and 6,241,777 B1 (both to Kellan), the entire contents of which are incorporated herein by reference. The amount of movement of the optic in these single-lens systems, however, may be insufficient to allow for a useful range of accommodation. In addition, as described in U.S. Pat. Nos. 6,197,059, 5,674,282, 5,496,366 and 5,476,514, the eye must be paralyzed for one to two weeks in order for capsular fibrosis to entrap the lens and thereby provide for a rigid association between the lens and the capsular bag. In addition, the commercial models of these lenses are made from a hydrogel or silicone material. Such materials are not inherently resistive to the formation of posterior capsule opacification ("PCO"). The only treatment for PCO is a capsulotomy using a Nd:YAG laser that vaporizes a portion of the posterior capsule. Such destruction of the posterior capsule may destroy the mechanism of accommodation of these lenses.

There have been some attempts to make a two-optic accommodative lens system. For example, U.S. Pat. No. 5,275,623 (Sarfarazi), WIPO Publication No. 00/66037 (Glick, et al.) and WO 01/34067 A1 (Bandhauer, et al), the entire contents of which are incorporated herein by reference, all disclose a two-optic lens system with one optic having a positive power and the other optic having a negative power. The optics are connected by a hinge mechanism that reacts to movement of the ciliary muscle to move the optics closer together or further apart, thereby providing accommodation. In order to provide this "zoom lens" effect, movement of the ciliary muscle must be adequately transmitted to the lens system through the haptics connecting the anterior lens to the posterior lens. Providing sufficient movement for a relatively broad range of accommodation through this mechanism has proven difficult.

Prior art accommodative two lens systems using a movable "zoom" lens have inherently limited movement. The maximum sensitivity or movement magnification $\alpha$ (a unitless ratio) is defined as the axial movement of the lens per unit zonule movement and is derived by the following equation:

$$\alpha = -B/A$$

where B is the projected distance of the zonule length which is in the order of 1.0 to 2.0 mm; and A is the axial distance between the middle plane between the dual lens and the anterior surface of the anterior lens where the zonules terminate.

Practically speaking, because of the lens thickness and dual lens separation requirement, A cannot be less than ~1 mm. Therefore, $\alpha$ cannot be larger than 2, which defines the limit of the known dual lens accommodative approaches. This limit is too low for the dual optics design to achieve the objective of creating the greater than 2.25 diopters of accommodative amplitude that patients need for normal accommodation, which ideally results in $\alpha$ greater than or equal to 4.

Therefore, a need continues to exist for a safe and stable dual lens accommodative intraocular lens that provides a relatively large amount of accommodative amplitude with minimal movement of the lenses.

BRIEF SUMMARY OF THE INVENTION

The present invention improves upon the prior art by providing embodiments of a two optic accommodative lens system wherein at least one of the optics is deformable. When compressed by the capsular bag, the two optics are pressed against each other, deforming at least one of the optics. As a result, the interface where the two optics meet changes shape, thereby altering the refractive power of the lens system. Such a lens system requires very little relative movement of the optics and low movement forces.

One embodiment of the present invention provides an intraocular lens, comprising a first lens having a first optic attached to a first peripheral ring by a plurality of haptics, and a second lens having a second optic attached to a second peripheral ring, the second peripheral ring sized and shaped to received the first peripheral ring so that the first optic is in contact with the second optic, wherein the haptics bias the first optic against the second optic. The second optic can likewise be attached to the second peripheral ring by a different plurality of haptics. To provide for deformation of at least one of the optics, and thus for the change in shape of the interface/area where the two optics are in contact, at least one of the optics is more compliant than the other. For example, the first optic can be more compliant than the second optic.

Further, in the embodiments of the present invention the intraocular lens can be such that the first optic is in contact with the second optic at a first area of the first optic when the intraocular lens is in a relaxed state, and the first optic is in contact with the second optic at a second area of the first optic when the intraocular lens is in a compressed state, the first area being smaller than the second area. The relaxed state can be an accommodative state of an eye in which the intraocular lens is implanted, and the compressed state can be a disaccomodative state of the eye in which the intraocular lens is implanted.

DETAILED DESCRIPTION OF THE INVENTION

The power of a lens surface is primarily determined by two physical parameters, the difference in refractive indices between the lens and the media in which the lens is submersed (e.g., air or aqueous humor) and the radius of curvature of the lens surface. Each of these parameters affect how much light rays are bent at the lens surface and therefore, determine the optical power of the lens.

Figure 1:
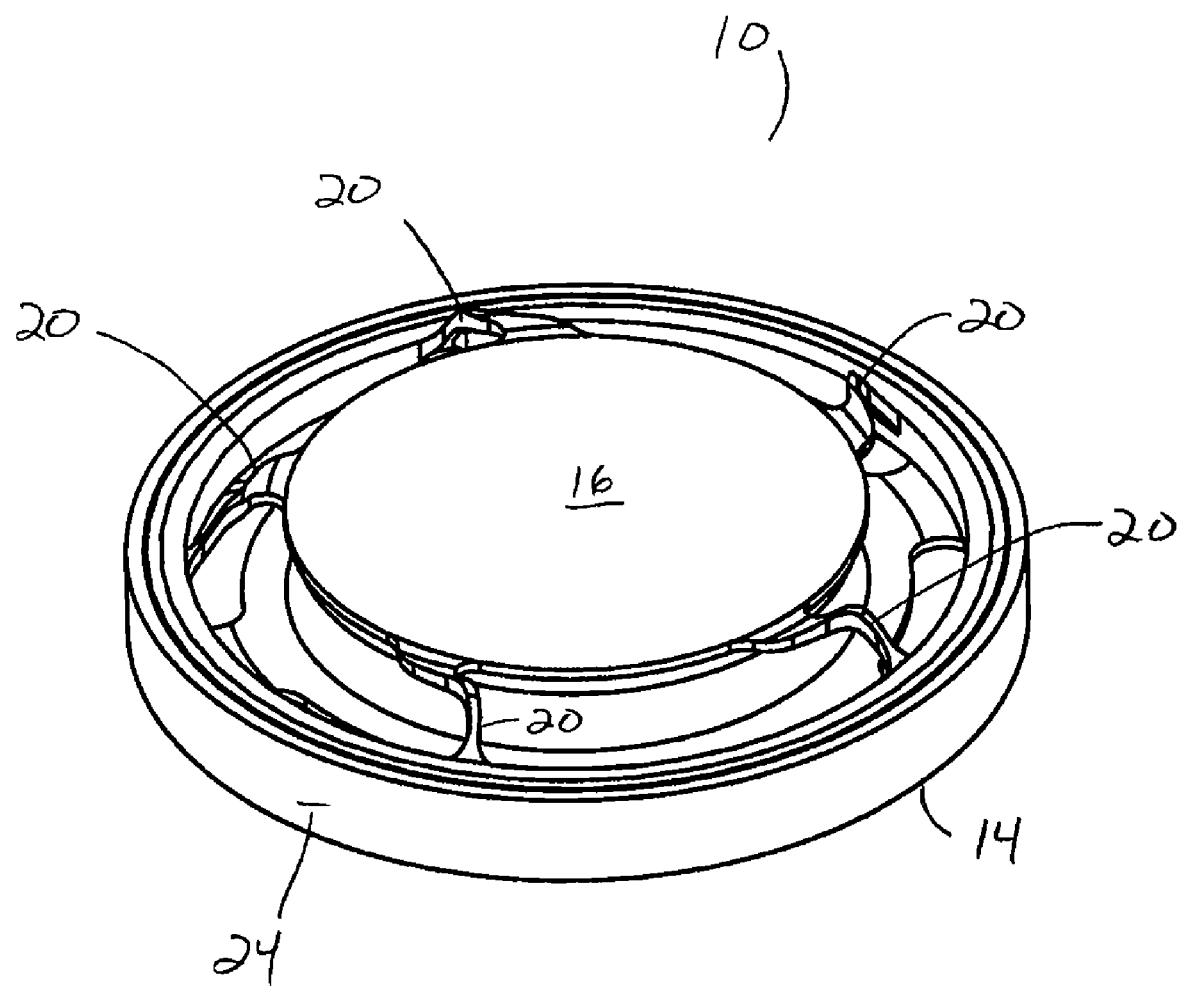
FIG. 1 is an enlarged perspective view of the lens system of the present invention.
Figure 2:
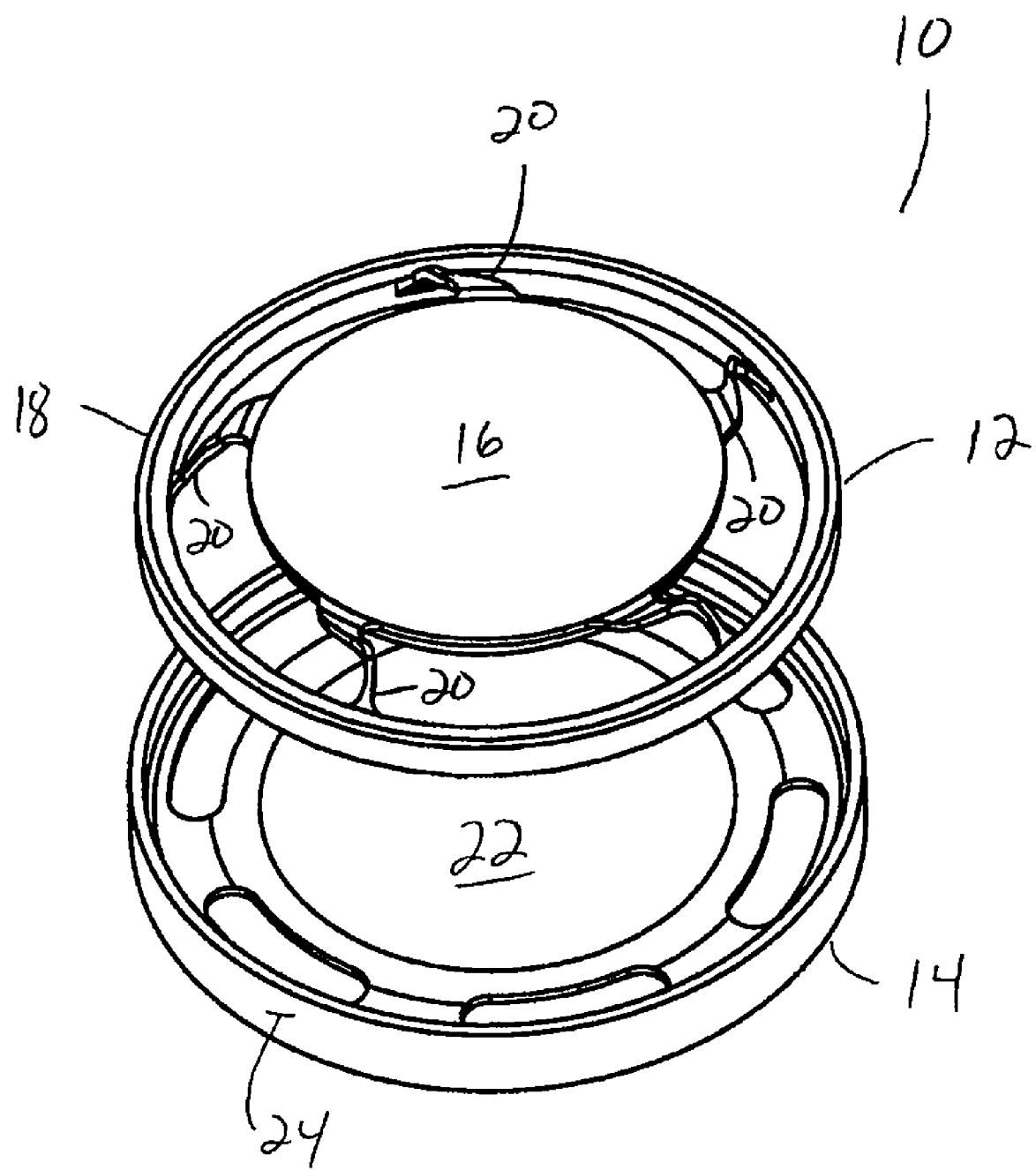
FIG. 2 is an enlarged exploded perspective view of the lens system of the present invention.

As best seen in FIGS. 1 and 2, lens system 10 of one embodiment of the present invention generally consists of anterior lens 12 and posterior lens 14. Anterior lens 12 contains anterior optic 16 connected to anterior peripheral ring 18 by a plurality of haptics 20. Anterior lens 12 can be made in a single piece from a deformable material such as silicone, hydrogel or soft acrylic. Posterior lens 14 contains anterior optic 22 which can be connected to and integrally formed with posterior peripheral ring 24. Posterior lens 14 can be made in a single piece from a deformable material such as silicone, hydrogel or soft acrylic having a refractive index different from anterior lens 12. Anterior peripheral ring 18 is sized and shaped so as to fit within posterior peripheral ring 24, so that anterior lens 12 nests within posterior lens 14. Haptics 20 bias first optic 16 against second optic 22.

Figure 3:
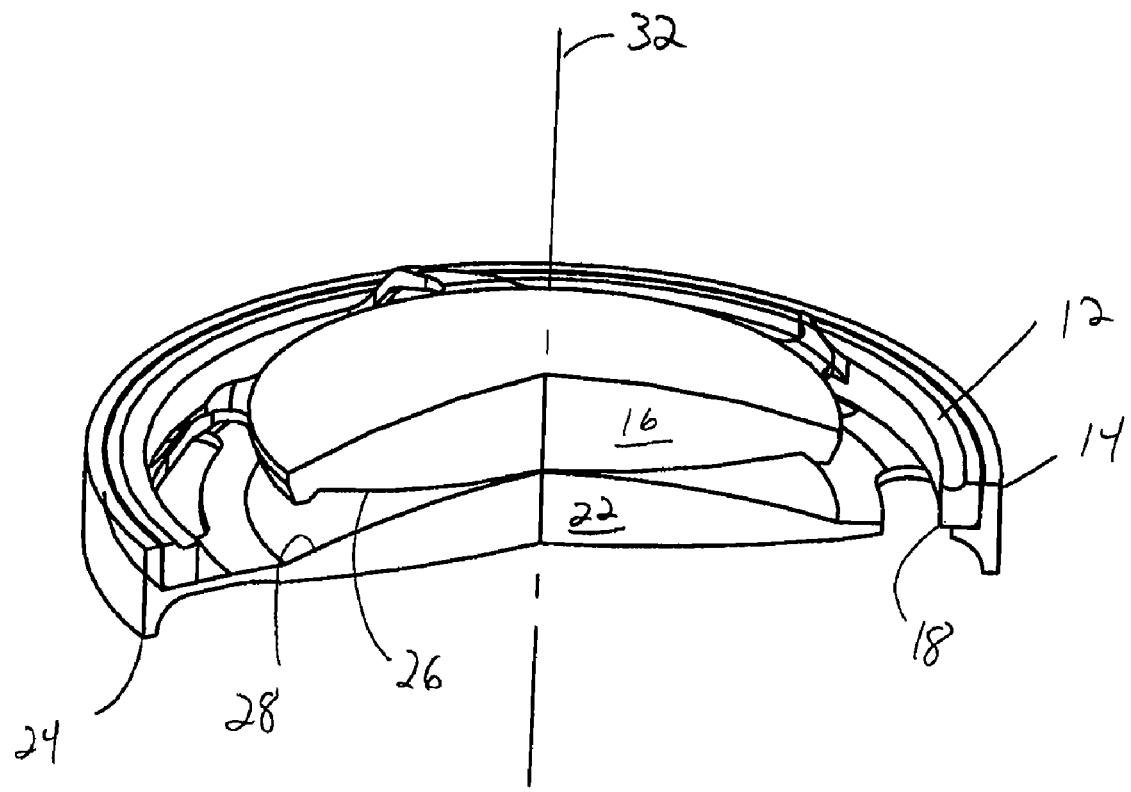
FIG. 3 is an enlarged cross-sectional view of the lens system of the present invention showing the optics in a relaxed state.

As best seen in FIG. 3, when the eye is in its accommodative state (the ciliary muscles relaxed), the capsular bag is flaccid, and anterior optic 16 and posterior optic 22 can expand to full thickness. In this relaxed state, optic 16 and optic 22 touch in a small area centered on optical axis 32, and the space between optic 16 and optic 22 is filled with aqueous humor, which has a refractive index different that either optic 16 or optic 22. Light passing through lens system 10 is bent at the interface of posterior side 26 of anterior optic 16 with the aqueous humor and again at the interface of anterior side 28 of posterior optic 22 with the aqueous humor.

Figure 4:
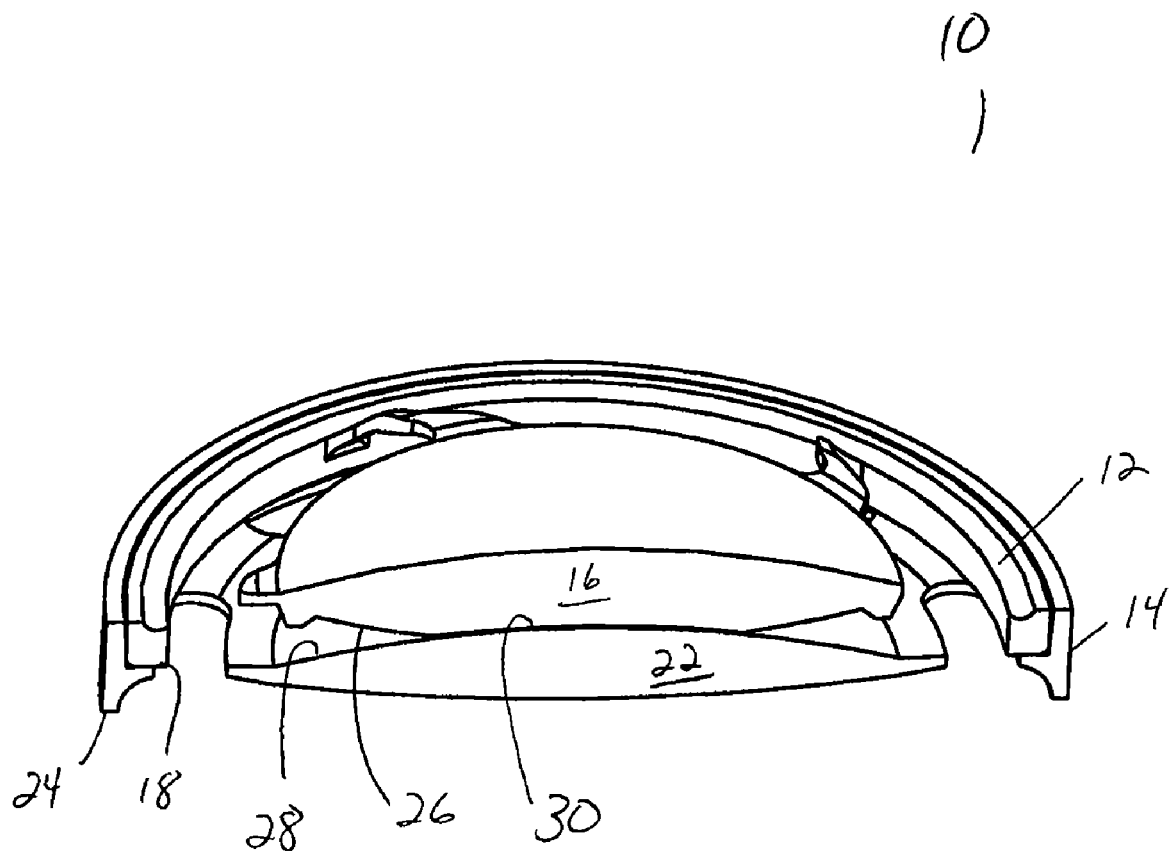
FIG. 4 is an enlarged cross-sectional view of the lens system of the present invention showing the optics in a compressed state.

When the eye is in a disaccommodative state, the ciliary muscles tighten, producing peripheral tension on the capsular bag equator. Such tension causes the anterior and posterior capsular membranes to move toward each other, compressing anterior optic 16 and posterior optic 22 against each other, as best seen in FIG. 4. Such compression causes anterior optic 16 and posterior optic 22 to press against one another, causing deformation of posterior side 26 of anterior optic 16, and to some extent, deformation on anterior side 28 of posterior optic 22, as anterior optic 16 can be less stiff (more compliant) than posterior optic 22. Anterior lens 12 presses against posterior lens 14 because of the interlocking nature of rings 18 and 24 and the shape of haptics 20, which tend to push anterior optic 16 posteriorly when compressed. Such deformation generally is contained within central 2 mm-3 mm zone 30 of optics 16 and 22, so that a small force is able to cause such deformation. Also, because any aqueous humor previously located between optic 16 and optic 22 in zone 30 is expelled, in zone 30 only the difference between the indices of refraction between optic 16 and optic 22, as well as the change in shape of posterior side 26 of anterior optic 16 and anterior side 28 of posterior optic 22, cause any bending of light passing through lens system 10. In addition, the optical powers of optics 16 and 22 outside of zone 30 are largely unaffected, resulting in lens system 10 having bi-focality. An important feature of lens system 10 is that deformation of zone 30 occurs very gradually, resulting in a gradual change in optical power.

This description is given for purposes of illustration and explanation. It will be apparent to those skilled in the relevant art that changes and modifications may be made to the invention described above without departing from its scope or spirit.

We claim:

1. An accommodative intraocular lens, comprising:
   a first lens having a first optic having a first interface attached to a first peripheral ring by a first plurality of haptics, wherein the first optic, the first peripheral ring and the first plurality of haptics are formed as a single piece;
   a second lens having a second optic having a second interface attached to a second peripheral ring by a second plurality of haptics, the second peripheral ring sized and shaped to receive the first peripheral ring so that the first interface region is in contact with the second interface region centered on an optical axis of the first optic thereby altering the refractive power of the lens and wherein the second optic, the second peripheral ring and the second plurality of haptics are integrally formed as a single piece;
   wherein the first plurality of haptics bias the first optic against the second optic.

2. The intraocular lens of claim 1, wherein the first optic is more compliant than the second optic.

3. The intraocular lens of claim 1, wherein the intraocular lens is configured such that the area of contact between the first optic and the second optic is smaller when the intraocular lens is in a relaxed state than when the intraocular lens is in a compressed state.

4. The intraocular lens of claim 1, wherein the intraocular lens is configures such that the area of contact between the first optic and the second optic is smaller when an eye in which the intraocular lens is implanted is in an accommodative state than when the eye is in a non-accommodative state.

5. The intraocular lens of claim 1, wherein a combined optical power of the first optic and the second optic changes at the area of contact in relation to the size of the area of contact and together with the non-contacting areas of the first and second optics provides a degree of bifocality.

* * * * *